US010174130B2

(12) United States Patent
Derez et al.

(10) Patent No.: US 10,174,130 B2
(45) Date of Patent: Jan. 8, 2019

(54) PROCESS FOR STARCH LIQUEFACTION

(71) Applicant: Cargill, Incorporated, Wayzata, MN (US)

(72) Inventors: Frank Derez, Sint-Pieters-Leeuw (BE); Jos Willy Ghislain Corneel De Sadeleer, Holsbeek (BE); Joost Ketsman, Oudenaarde (BE); Luigi Nataloni, Bologna (IT)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 14/370,329

(22) PCT Filed: Aug. 7, 2013

(86) PCT No.: PCT/US2013/053929
§ 371 (c)(1),
(2) Date: Jul. 2, 2014

(87) PCT Pub. No.: WO2014/025872
PCT Pub. Date: Feb. 13, 2014

(65) Prior Publication Data
US 2015/0166684 A1 Jun. 18, 2015

(30) Foreign Application Priority Data
Aug. 9, 2012 (EP) .................................... 12005775

(51) Int. Cl.
*C12P 19/14* (2006.01)
*C08B 30/08* (2006.01)
*C08B 30/12* (2006.01)
*C08B 30/14* (2006.01)
*C08B 30/18* (2006.01)
*C12P 19/22* (2006.01)
*C13K 1/06* (2006.01)
*C12P 19/02* (2006.01)

(52) U.S. Cl.
CPC .............. *C08B 30/08* (2013.01); *C08B 30/12* (2013.01); *C08B 30/14* (2013.01); *C08B 30/18* (2013.01); *C12P 19/02* (2013.01); *C12P 19/14* (2013.01); *C12P 19/22* (2013.01); *C13K 1/06* (2013.01)

(58) Field of Classification Search
CPC ......... C08B 30/12; C08B 30/14; C08B 30/18; C08B 30/08; C12P 19/02; C12P 19/22; C12P 19/14; C13K 1/06
See application file for complete search history.

(56) References Cited

U.S. PATENT DOCUMENTS

| 3,819,484 A | 6/1974 | Okada et al. |
| 3,849,194 A | 11/1974 | Armbruster et al. |
| 3,853,706 A | 12/1974 | Armbruster |
| 3,974,034 A | 8/1976 | Horn et al. |
| 4,014,743 A * | 3/1977 | Black ...................... C12P 19/14 435/184 |
| 4,062,728 A | 12/1977 | Blanchard |
| 4,235,965 A | 11/1980 | Walon |
| 4,298,400 A | 11/1981 | Armbruster |
| 4,335,208 A | 6/1982 | Norman |
| 4,376,163 A | 3/1983 | Ehnstroem |
| 4,410,368 A | 10/1983 | Takasaki et al. |
| 5,886,198 A | 3/1999 | Brumm |
| 6,184,002 B1 | 2/2001 | Mitchinson et al. |
| 6,448,049 B1 | 9/2002 | Tsutsumi et al. |
| 6,642,044 B2 | 11/2003 | Svendsen et al. |
| 7,915,020 B2 * | 3/2011 | Cates ................. C12N 15/8242 435/161 |
| 2003/0134396 A1 | 7/2003 | Sketty et al. |
| 2008/0118957 A1 | 5/2008 | Deleyn et al. |
| 2008/0121227 A1 * | 5/2008 | Bhargava ................. C12P 7/06 127/46.1 |
| 2011/0178288 A1 | 7/2011 | Deleyn et al. |

FOREIGN PATENT DOCUMENTS

| EP | 0806434 A1 | 11/1997 |
| GB | 1200817 A | 8/1970 |
| JP | S395438 B | 4/1964 |
| JP | S4919049 A | 2/1974 |
| JP | S4926438 A | 3/1974 |
| JP | H09149782 A | 6/1997 |
| RU | 2421525 C1 | 6/2011 |
| WO | 1993009244 A1 | 5/1993 |
| WO | 2006047176 A1 | 5/2006 |

OTHER PUBLICATIONS

Carr M.E. et al., "Continuous Enzymatic Liquefaction of Starch for Saccharification", Biotechnology and Bioengineering, 1982, vol. XXIV, pp. 2441-2449. (Year: 1982).*
International Search Report of PCT/US2013/053929, dated Sep. 4, 2013, 3 pages.
International Search Report dated Mar. 30, 2006 for PCT/US2005/037592 filed Oct. 21, 2005 (2 pages).

* cited by examiner

*Primary Examiner* — Satyendra K Singh

(57) ABSTRACT

The present invention relates to a process for the liquefaction of starch present in a starch slurry comprising degraded starch and having a DE of from 0.05 to 9. Preferably, the invention relates to a process for the liquefaction of starch present in a starch slurry comprising degraded starch, said starch slurry having a high dry substance. Further preferably, the invention relates to a continuous process for liquefaction of starch present in a starch slurry comprising degraded starch and having a high dry substance.

13 Claims, No Drawings

PROCESS FOR STARCH LIQUEFACTION

CROSS REFERENCE TO RELATED APPLICATION

This application is a national phase application of International Application PCT/US2013/053929, entitled PROCESS FOR STARCH LIQUEFACTION, filed Aug. 7, 2013, which claims the benefit of the European Provisional Patent Application, Serial No. 12005775.7, entitled PROCESS FOR STARCH LIQUEFACTION, filed Aug. 9, 2012, which is hereby incorporated by reference in its entirety.

FIELD OF THE INVENTION

The present invention relates to a process for the liquefaction of starch present in a starch slurry comprising degraded starch and having a DE of from 0.05 to 9. Preferably, the invention relates to a process for the liquefaction of starch present in a starch slurry comprising degraded starch, said starch slurry having a high dry substance. Further preferably, the invention relates to a continuous process for liquefaction of starch present in a starch slurry comprising degraded starch and having a high dry substance.

BACKGROUND OF THE INVENTION

Native starch, i.e. starch recovered in its original form by extraction from any starch-bearing material, is a starting material for numerous valuable products. Starch hydrolysis process can yield glucose syrups, high maltose syrups, very high maltose syrups and the like. From these syrups, several products can be obtained such as crystalline dextrose, polyols and the like.

The process to hydrolyse starch typically comprises liquefaction and saccharification of native starch in the form of a starch slurry. Starch is a natural ingredient with a typical behaviour when it is put into suspension (starch slurry). Above a certain dry substance, the slurry is very difficult to treat and can be responsible for blocking processing equipment. Therefore in current processes, starch slurry to be liquefied typically has a dry substance up to 40 weight/weight % (w/w %) and preferably of from 30 to 35 w/w %. Taking into account heating via steam injection for the liquefaction and subsequent flashing for the saccharification, the liquefact thus produced also has a comparable dry substance. However it is desirable to increase this dry substance, for reasons of microbial stability, cost, process efficiency and the like. At least one additional concentration step, typically by evaporation, is necessary to bring the dry substance content of the produced glucose syrups to the desired value, such as for example 60 w/w %, 70 w/w %, 80 w/w %, 85 w/w %, etc. This concentration step usually requires a high energy input and is therefore not cost efficient and not environmentally friendly. In the effort to reduce energy consumption of industrial processes, there is a need to provide a more efficient process with significant lower energy consumption.

EP 0806434A1 describes a batch process for preparing enzyme converted starches.

U.S. Pat. No. 4,235,965 describes a batch process to hydrolyse starch, starting from a starch slurry having a dry substance of up to 40 w/w %. The process is a non-continuous batch process and requires very high amounts of enzymes, consequently the process is relatively inefficient and very costly.

There is thus a need for a starch liquefaction process with a higher capacity and better energy balance that preferably runs continuously. The present invention provides for such a starch liquefaction process.

SUMMARY OF THE INVENTION

The present invention relates to a process for the liquefaction of starch present in a starch slurry, wherein said starch slurry has a DE of from 0.05 to 9 and comprises degraded starch.

DETAILED DESCRIPTION

The present invention relates to a process for the liquefaction of starch present in a starch slurry, wherein said starch slurry has a DE of from 0.05 to 9 and comprises degraded starch.

Conventional starch hydrolysis processes typically comprise a liquefaction step followed by a saccharification step In such processes, the starch slurry entering the liquefaction step has a dry substance of up to 40 weight/weight % (w/w %). Above this dry substance, the starch slurry is the starch comprises native starch. In conventional processes, starch slurry consists essentially of native starch. For this reason, the dry substance of the starch slurry is kept at a value of maximum 40 w/w %, typically of from 30 w/w % to 35 w/w %.

Liquefaction is done at high temperatures, by direct heating to 80 to 160° C., preferably to 90 to around 110° C. through steam injection, wherein said steam has a pressure of from 9 to 12 bar. At these temperatures, the starch gelatinizes and viscosity increases. For this reason also, it is necessary to keep the dry substance content of the starch slurry at values of from 30 w/w % to 35 w/w %. Also it is necessary to heat by steam injection, i.e. direct heating, which results in a very fast heating of the starch slurry and which limits the increase in viscosity and allows a good starch liquefaction. When heating would be done by indirect heating, the starch would have time to gelatinize and the viscosity increase would be too important and would render pumping and further processing very complicated.

During liquefaction, the starch present in the starch slurry is broken down into dextrose oligomers, typically through the action of enzymes. After liquefaction, the liquefied starch slurry (the liquefact) is saccharified, typically through the action of saccharification enzymes, to yield dextrose containing liquors, maltose containing liquors and the like.

For the purpose of the present invention, the botanical origin of the starch is not restricted. Suitable sources of starch for use in the present invention are corn, pea, potato, sweet potato, sorghum, banana, barley, wheat, rice, sago, amaranth, tapioca, arrowroot, canna, and low amylose (containing no more that about 10% by weight amylose, preferably no more than 5% by weight amylose) or high amylose (containing at least about 40% by weight amylose) varieties thereof. Genetically modified varieties of these crops are also suitable sources of starch. Preferably however, starch is derived from cereals, more preferably from wheat and/or corn. The tem starch used as such means for the purpose of the present invention native starch. It is well known in the art how to extract native starch from above mentioned plants. It does not however exclude in any of the process steps of the present invention that modified starch can be added. Modified starch refers to starch chemically modified, enzymatically modified, modified by heat treatment or by physical treatment. The term "chemically modified"

includes, but is not limited to crosslinking, modification with blocking groups to inhibit retrogradation, modification by the addition of lipophilic groups, acetylated starches, hydroxyethylated and hydroxypropylated starches, inorganically esterified starches, cationic, anionic and oxidized starches, zwitterionic starches, starches modified by enzymes and combinations thereof. Heat treatment includes for example pregelatinization.

According to the process of the present invention, the starch slurry entering the liquefaction step already comprises degraded starch. It is understood for the purpose of the present invention that degraded starch results from acid and/or enzymatic hydrolysis of starch and can be one or more of maltodextrins, dextrose, dextrose oligomers, maltose and the like, such products being soluble in water.

The starch slurry entering the liquefaction step can be obtained by a process comprising:
1. Providing a first starch slurry
2. Pre-liquefying the first starch slurry to obtain a pre-liquefact and
3. Optionally adding starch and/or one or more starch degrading enzymes to the pre-liquefact to obtain a second starch slurry, said second starch slurry is the starch slurry which will be sent to the liquefaction step.

The first starch slurry can prepared for example by mixing native starch with water to obtain a slurry having a dry substance of from 25 w/w % to 45 w/w %, preferably 30 w/w % to 45 w/w %, more preferably 35 w/w % to 45 w/w % even more preferably 40 w/w % to 45 w/w %, yet even more preferably above 40 w/w % to 45 w/w %. The starch can be in dry powder form or in the form of a slurry. The starch can have a dry substance of from 40 w/w % to 90 w/w %. Preferably, the starch is native starch having a dry substance of from 80 w/w % to 90 w/w %.

The pre-liquefact is in fact the first starch slurry which now comprises degraded starch, either because degraded starch has been added to the first starch slurry, or because part of the native starch of the first starch slurry has been degraded. The pre-liquefact has a DE (Dextrose Equivalent) of about 0.05 to about 9, preferably of from 0.05 to 8, preferably of from 0.05 to 7, more preferably of from 0.05 to 6, even more preferably of from 1 to 5. The DE can be measured with Lane Eynon official method. Preferably, the pre-liquefact has a solubility level of at least 3, preferably at least 6, more preferably of at least 10, even more preferably of at least 20. The solubility level is an indication of the amount of starch that is degraded thus solubilized. The solubility level of the pre-liquefact is measured according to test A as described in the measurement methods section of this description.

The pre-liquefact has a similar dry substance as the first starch slurry, i.e. from 25 w/w % to 45 w/w %, preferably 30 w/w % to 45 w/w %, more preferably 35 w/w % to 45 w/w % even more preferably 40 w/w % to 45 w/w %, yet even more preferably above 40 w/w % to 45 w/w %.

Pre-liquefaction of the first starch slurry to obtain a pre-liquefact can be done by adding degraded starch, as defined above, to the first starch slurry. Said degraded starch can be either in powder foam and/or in the form of a solution. In this case, providing a first starch slurry and pre-liquefying the first starch slurry can also be done in one single step, by mixing degraded starch with native starch and water. The degraded starch can be in powder form and/or in the form of a solution and the native starch can be in powder form and/or in the form of a slurry. Alternatively, and preferably, degraded starch is produced 'in situ' by acid and/or enzymatic pre-liquefaction of the first starch slurry.

Preferably the pre-liquefaction comprises an enzymatic treatment at a temperature of from 20 to 85° C., typically said temperature is below or maximum 10° C. above the gelatinization temperature of the native starch used to prepare the first starch slurry.

Enzymatic pre-liquefaction comprises adding one or more starch degrading enzymes to the first starch slurry. The one or more enzymes can be for example an α-amylase, a β-amylase, a glucoamylase, a pullulanase or a combination of these. The quantity of enzyme to be added, will easily be determined by the person skilled in the art, such as to obtain a pre-liquefact, having a DE of from 0.05 to 9. Preferably such as to obtain a pre-liquefact further having a solubilisation level of at least 3, preferably at least 6, more preferably of at least 10, even more preferably of at least 20.

Enzymatic pre-liquefaction is preferably done at a temperature of from 20° C. to 85° C., more preferably from 25° C. top 75° C., even more preferably from 30° C. to 70° C. and most preferably from 35° C. to 60° C. For example, the first starch slurry can have an initial temperature of from 40° C. to 50° C.

Preferably the first starch slurry is first brought to a pH value optimal for the enzyme or enzyme cocktail used. Typically, a pH of from 5 to 6.5 is used for common α-amylases. The pH can be modified with any suitable method known in the art, for example by the addition of acid or base depending on whether the initial pH is lower or higher than the desired pH value. The skilled person will easily know how to adapt the pH of the first starch slurry.

The pre-liquefaction is preferably done in a reactor. Any type of suitable reactor can be used such as for example a tank, plug flow reactor, and the like, with or without agitator, with or without prop flow. Preferably, a closed reactor having one or more inlets and one or more outlets can be used. The one or more inlets and the one or more outlets can be situated on the upper and/or lower side of the reactor. Both inlet and outlet are such that the inflow and the outflow of the reactor can be regulated easily manually or automatically.

Through the action of the enzymes, the first starch slurry is converted into a starch slurry comprising degraded starch, thus the pre-liquefact, as defined above.

The pre-liquefact can be sent to the liquefaction step as follows: part of the pre-liquefact is removed from the reactor and sent towards a liquefaction step and the removed part is replaced with starch, preferably native starch, to maintain the slurry in the reactor at a dry substance of from 25 w/w % to 45 w/w %, preferably 30 w/w % to 45 w/w %, more preferably 35 w/w % to 45 w/w % even more preferably 40 w/w % to 45 w/w %, yet even more preferably above 40 w/w % to 45 w/w %; or to increase its dry substance to up to 80 w/w %.

Before the liquefaction step, an additional step can be performed. For example this additional step can comprise the addition of an enzyme and adjusting temperature and/or pH if required.

Preferably, the step of removing part of the liquefact and sending it towards a liquefaction step and replacing the removed part with starch or with starch and enzyme is done simultaneously, at the same rate and preferably continuously, without substantial interruption during the process. At this point the process can start running in a continuous way. For the purpose of the present invention continuous means without substantial interruption during the process time. Said process time can be from 5 minutes to multiple hours.

Preferably however, once the pre-liquefact is obtained, starch can be added to it, in order to increase its dry substance to a value of from 30 w/w % to 80 w/w %. Preferably starch comprises native starch, more preferably starch consists of native starch. Starch can also be added simultaneously with the one or more pre-liquefaction enzymes.

Thus, the process of the present invention is further preferably characterized in that it comprises the steps of:
a. Providing in a reactor a pre-liquefact at a dry substance of from 25 w/w % to 45 w/w %; and
b. Adding starch, preferably native starch, in a reactor containing the pre-liquefact at a temperature of from 20 to 85° C., to obtain a second starch slurry having a dry substance of from 30 w/w % to 80 w/w %; and
c. Removing part of the second starch slurry from the reactor and sending it towards a liquefaction step and replacing the removed part with starch, preferably native starch, to maintain the second starch slurry in the reactor at a dry substance of from 30 w/w % to 80 w/w %.

Preferably further, in step b. and/or step c. one or more starch degrading enzymes can also be added.

The starch and the one or more starch degrading enzymes in step b. and/or step c. can be mixed together prior to addition or they can be added separately, simultaneously or in sequence. Further, they can be added in several steps or continuously. Preferably, they are added simultaneously, continuously, i.e. without substantial interruption from the start of addition to the end of addition, without prior mixing.

Thus preferably, the present invention relates to a process for the liquefaction of starch present in a starch slurry characterized in that said starch slurry
comprises degraded starch material obtained by pre-liquefaction of a first starch slurry, said pre-liquefaction comprising enzymatic treatment at a temperature of from 20 and 85° C., and
has a dry substance of from 30 w/w % to 80 w/w %.

The second starch slurry, i.e. the starch slurry to be liquefied, can have a dry substance of from 30 w/w % up to 80 w/w %, preferably of from 35 w/w % to 80 w/w %. Preferably, the second starch slurry has a high dry substance: from 40 w/w % to 80 w/w %, more preferably above 40 to 70 w/w %, even more preferably from 45 w/w % to 60 w/w %, yet even more preferably of from 45 w/w % to 55 w/w %, and yet even more preferably of from 48 w/w % to 52 w/w % or from 50 w/w % to 55 w/w %. Due to the presence of the degraded starch, the dry substance of the second starch slurry can be higher than in conventional processes where only native starch is used, without facing the process limitations described earlier.

Preferably, one or more starch degrading enzymes, as defined above are also added in step b. and or step c. Preferably, enzyme with optimal working conditions at pH 3.5 to 6.5 is chosen. The quantity of enzyme to be added, will easily be determined by the person skilled in the art, and should be such as to maintain the DE of the starch slurry in the reactor at a value of from 0.05 to 9. Preferably such as to maintain the solubility index of the starch slurry in the reactor at a value of at least 3, preferably at least 6, more preferably of at least 10, even more preferably of at least 20. Preferably further, the one or more starch degrading enzymes are thermostable, such as to resist the heating step in a subsequent liquefaction step.

The starch and the one or more starch degrading enzymes, if any, can be mixed together prior to addition or they can be added separately, simultaneously or in sequence. Further, they can be added in several steps or continuously. Preferably, they are added simultaneously, continuously, i.e. without substantial interruption from the start of addition to the end of addition, without prior mixing.

The temperature in the reactor is maintained at a value of from 20 to 85° C., preferably more preferably from 25 to 75° C., even more preferably from 30 to 70° C. and even more preferably from 35 to 60° C. The temperature can be maintained by any method known in the art such as by the use of a double jacketed reactor having water circulating at the right temperature, such as to maintain the content of the reactor at the desired temperature.

Preferably, the second starch slurry in the reactor is mixed. Mixing can be achieved with any suitable method known in the art, such as with a static mixer for example.

The pH of the second starch slurry depends on the one or more starch degrading enzyme that is used. The person skilled in the art will easily know which pH should be obtained depending on the enzyme used. Preferably, an enzyme with optimal working conditions at pH 3.5 to 6.5 is chosen.

The viscosity of the second starch slurry is lower than the viscosity of a starch slurry comprising essentially native starch at the same dry substance, temperature and pH. This viscosity lowering effect allows processing a starch slurry having a higher dry substance, compared to conventional liquefaction processes, as explained above.

Part of the second starch slurry is removed from the reactor via an outlet of the reactor and is sent towards a liquefaction step. The removed part is replaced by starch or by starch and starch degrading enzyme (replacing material), in order to maintain the dry substance of the second starch slurry at a value of from 30 w/w % to 80 w/w %. Preferably, removing and replacing is done at such a rate as to obtain an average retention time of the second starch slurry in the reactor of from 5 minutes to 5 hours, preferably from 30 minutes to 3 hours, more preferably form 2 hour to 3 hours. Preferably, removing and replacing of the second starch slurry is done simultaneously. Preferably, the amount of second starch slurry that is removed is equal to the amount of replacing material that is added, such that the dry substance of the second starch slurry in the reactor does not vary, but is maintained at a same value which is, as explained above, from 30 w/w % to 80 w/w %. More preferably, the step of removing part of the second starch slurry and sending it towards a liquefaction step and replacing the removed part with starch or with starch and enzyme is done continuously, without substantial interruption during the process. At this point the process is running in a continuous way. Thus, more preferably once the pre-liquefact is obtained and its dry substance has been increased to yield the second starch slurry, the process runs in a continuous way: starch or starch and enzymes are continuously added into the reactor and part of the second starch slurry is continuously sent to liquefaction, thus step c. of the process is repeated. For the purpose of the present invention continuous means without substantial interruption during the process time. Said process time can be from 5 minutes to multiple hours.

Optionally, before the liquefaction step, an additional step can be performed. For example this additional step can comprise the addition of an enzyme and adjusting temperature and/or pH if required.

Liquefaction is a well-known process in the starch industry and the liquefaction conditions (time, temperature and the like) will be apparent to the person skilled in the art. During the liquefaction, the second starch slurry is typically brought to a temperature of from 90 to 255° C., preferably of from 90 to 150° C., more preferably of from 90 to 130°

C., even more preferably of from 90 to 110° C. Heating can be done by direct steam injection in a jet cooker. Surprisingly, with the process of the present invention, heating can also be done by indirect heating.

Liquefaction by steam injection has the disadvantage of adding water in the starch slurry. This extra water will have to be removed from the liquefact at a later stage of the process. This requires energy and is not cost friendly, not efficient and not environmentally friendly. It has surprisingly been found that the presence of degraded starch in the starch slurry entering the liquefaction has the advantage that heating during the liquefaction can be done by indirect heating, for instance by means of a compabloc. Indirect heating does not add water to the starch slurry, removing the disadvantage listed above. Indirect heating can be done by any suitable method known in the art. Thus the process of the present invention is further characterized in that the liquefaction stepis done by indirect heating of the second starch slurry at temperature of from 90 to 255° C., preferably from 90 to 150° C., more preferably from 90 to 130° C., even more preferably from 90 to 110° C.

After the liquefaction, saccharification can be done. The liquefied starch is broken down into dextrose through the action of saccharification enzymes, such as glucoamylase or amyloglucosidase. After saccharification, a high dextrose containing liquor is obtained, having a dry substance similar to or somewhat higher (due to chemical gain) than that of the second starch slurry, i.e. a dry substance of from 40 w/w % to 80 w/w %. Thus the dextrose containing liquor obtained by the process of the present invention has a much higher dry substance than dextrose containing liquors obtained by conventional starch hydrolysis processes. Less water has to be removed to obtain dextrose syrups at a desired dry substance. Thus fewer to no evaporation steps may be required. Thereby a more cost efficient and more environmental friendly process is obtained. Optionally, dextrose can be recovered in the form of crystalline dextrose through crystallisation for example.

Alternatively, an isomerisation of dextrose can be done to yield fructose.

Alternatively, after liquefaction, a saccharification to maltose can be done. A maltose containing liquor is obtained which has a much higher dry substance compared to that of maltose liquors obtained by conventional processes. The maltose containing liquor has a dry substance similar to or somewhat higher (due to chemical gain) than that of the second starch slurry, i.e. a dry substance of from 40 w/w % to 80 w/w %. Also here, fewer to no evaporation steps may be required.

Additionally or alternatively, any other suitable treatment can be done after the liquefaction step.

Most preferably, the present invention relates to a process comprising:

in a reactor, submitting a first starch slurry at a dry substance of from 30 to 35 w/w % to an enzymatic pre-liquefaction at a temperature of from 20 to 85° C. to yield a pre-liquefact, and adding native starch and one or more starch degrading enzymes to the pre-liquefact, to obtain a second starch slurry having a dry substance of from 40 w/w % to 55 w/w %; and removing part of the second starch slurry from the reactor and sending it towards a liquefaction step and replacing the removed part with native starch and one or more starch degrading enzyme, to maintain the second starch slurry in the reactor at a dry substance of from 40 w/w % to 55 w/w %, and liquefying the removed part at a temperature of from 90 to 130° C. to yield a liquefact, and saccharifying the liquefied starch slurry to dextrose or maltose containing syrups.

Methods of Measurement

Test A: measurement of solubility level of a starch slurry comprising degraded starch. 100 ml of starch slurry comprising degraded starch at about 40° C. is filtered through a Macherey-Nagel (MN) 614 ¼ 150 mm diameter folded paper filter. The refractive index of the filtrate at 20° C. is measured with a refractometer ATAGO DR-A1. The refractometer derives the ° Brix value from the refractive index and this ° Brix corresponds to the solubility level.

EXAMPLES

Example 1

Liquefaction P110329

0.03 w/w % of α-amylase Spezyme Alpha PF from Genencor (previously known as GC358) is added to a first wheat starch slurry having a dry substance of 32 w/w % at 47° C., in a double jacketed tank. The pH is about 5.7.

The temperature is raised from 47° C. to 54° C. and maintained during 2 hours and 20 minutes. A pre-liquefact is obtained having a solubilisation level of 12.5%.

Then wheat starch (88% dry substance) is added gradually to obtain a second starch slurry having a dry substance of 51.6 w/w %. 0.03 w/w % α-amylase Spezyme Alpha PF and 0.034% α-amylase Liquozyme Supra 2.8× are also added gradually. This addition step is done in 30 minutes. The temperature is maintained during the whole time at 54° C. The solubilisation level of the second starch slurry is measured at 19.5%.

The second starch slurry is leaving the tank at a rate of 130 l/h. At the same time 90 kg/h of dry wheat starch (88% dry substance) and 73 l/h of water is added to the tank. At this point the process is running in a continuous way by adding fresh starch, enzymes and discharge the second starch slurry into a liquefaction step and this at a dry substance higher than what can be reached with the conventional process.

The second starch slurry leaving the tank has a temperature of 54° C. and is brought to a jet cooker where the temperature is increased to 107° C. by steam injection. It is then maintained at a temperature of 107° C. during 10 minutes and subsequently, after atmospheric flash, the temperature is reduced to about 98° C. The DE of the liquefact is measured at about 12 and the dry substance is about 48 w/w %.

Further liquefaction is achieved by collecting said liquefact during 60 minutes and holding during 60 minutes at 95° C. to 98° C. until a DE of 23.3 is obtained. The liquefact at this stage is starch negative and can be sent continuously to the further processing steps.

Example 2

Liquefaction P120131

0.01 w/w % of α-amylase Spezyme Alpha PF and 0.01 w/w % Liquozyme Supra 2.8× is added to a first wheat starch slurry having a dry substance of 44.7 w/w % at 35° C., in a double jacketed tank. The pH is about 5.6.

The temperature is maintained at 35° C. during 150 minutes. A pre-liquefact is obtained having a solubilisation level of 5.1%.

The pre-liquefact is leaving the tank at a rate of 130 l/h. At the same time a starch slurry of 45 w/w % dry substance is added to the tank at a rate of 130 l/h.

The pre-liquefact leaving the tank has a temperature of 35° C. and is sent continuously to a second tank. 0.0085% Liquozyme Supra 2.8× based on dry substance is added to the second tank. The average retention time in the second tank is 20 minutes. This mixture is brought continuously to a jet cooker where the temperature is increased to 107° C. by steam injection, it is then maintained at a temperature of 107° C. during 10 minutes and subsequently, after atmospheric flash, the temperature is reduced to about 98° C. The DE of this liquefact is measured at about 4.9 and the dry substance is about 42.3 w/w %.

Further liquefaction is achieved by collecting said liquefact during 45 minutes and holding during 15 minutes at 95° C. to 98° C. until a DE of 12.9 is obtained. This liquefact at this stage is starch negative and is sent in a continuous way to the further processing steps.

The invention claimed is:

1. A process for liquefying starch present in a starch slurry, comprising:
    a. Providing in a reactor a first starch slurry comprising degraded starch, wherein the first starch slurry has a dextrose equivalent (DE) of from 0.05 to 9 and a solubilisation level of at least 3; and
    b. Adding starch to the reactor containing the first starch slurry at a temperature of from 25 to 75° C., to obtain a second starch slurry having a dry substance of from 40 w/w % to 80 w/w %; and
    c. Removing a portion of the second starch slurry from the reactor and sending it towards a liquefaction step and replacing the removed portion with starch, wherein the starch consists of native starch, to maintain the second starch slurry in the reactor at a dry substance of from 40 w/w % to 80 w/w %;
    wherein the step c is repeated and performed in a continuous way.

2. The process according to claim 1, wherein the first starch slurry has a solubilisation level of at least 6.

3. The process according to claim 1, wherein the first starch slurry has a solubilisation level of at least 10.

4. The process according to claim 1, wherein the first starch slurry has a solubilisation level of at least 20.

5. The process according to claim 1, wherein the degraded starch is one or more of the maltodextrins, dextrose, and maltose.

6. The process according to claim 1, wherein the degraded starch is a pre-liquefact obtained by a pre-liquefaction comprising enzyme treatment, at a temperature between 20 and 75° C.

7. The process according to claim 1, wherein the starch added in step b and step c has a dry substance of from 40 w/w % to 90w/w %.

8. The process according to claim 1, wherein one or more starch degrading enzymes are added in step b or step c and wherein the starch added in step b comprises native starch.

9. The process according to claim 1, wherein the second starch slurry has a pH of from 3.5 to 6.5.

10. The process according to claim 1, wherein one or more starch degrading enzymes are added in step b and/or step c.

11. The process according to claim 1, wherein one or more starch degrading enzymes are added in step b or step c and wherein the starch degrading enzymes comprise α-amylase.

12. The process according to claim 1, wherein one or more starch degrading enzymes are added in step b and/or step c and wherein the second starch slurry has a pH of from 3.5to 6.5.

13. The process according to claim 1, additionally comprising the step of carrying out a liquefaction step on the removed portion of the second starch slurry by indirect heating and without steam injection.

* * * * *

UNITED STATES PATENT AND TRADEMARK OFFICE
CERTIFICATE OF CORRECTION

PATENT NO. : 10,174,130 B2
APPLICATION NO. : 14/370329
DATED : January 8, 2019
INVENTOR(S) : Frank Derez et al.

It is certified that error appears in the above-identified patent and that said Letters Patent is hereby corrected as shown below:

On the Title Page

In item "(56) References Cited", under "U.S. PATENT DOCUMENTS", Line 13, delete "5,886,198" and insert -- 5,886,168 --, therefor.

In the Specification

In Column 2, Line 60, delete "tem" and insert -- term --, therefor.

In Column 3, Line 59, delete "foam" and insert -- form --, therefor.

In the Claims

In Column 9, Line 33, in Claim 1, after "portion with", insert -- native --.

In Column 9, Lines 33-34, in Claim 1, after "starch,", delete "wherein the starch consists of native starch,".

Signed and Sealed this
Twenty-sixth Day of November, 2019

Andrei Iancu
*Director of the United States Patent and Trademark Office*